United States Patent [19]  [11] 4,252,569
Roedel  [45] Feb. 24, 1981

[54] PROCESS FOR PREPARING ALKALI METAL SILICONATES

[75] Inventor: George F. Roedel, Schenectady, N.Y.

[73] Assignee: General Electric Company, Waterford, N.Y.

[21] Appl. No.: 734,146

[22] Filed: Oct. 20, 1976

[51] Int. Cl.³ .............................................. C07F 7/04
[52] U.S. Cl. ............................................... 106/287.16
[58] Field of Search ............... 260/448.8 R, 46.5 R; 106/287 SB, 13, 12, 2, 287.16

[56] References Cited

U.S. PATENT DOCUMENTS

| | | | |
|---|---|---|---|
| 2,438,055 | 3/1948 | Hyde et al. | 106/287 SB |
| 2,556,897 | 1/1951 | Bidaud | 260/46.5 |
| 2,711,967 | 6/1955 | Tomarkin | 260/46.5 R |
| 3,008,975 | 11/1961 | Schubert | 260/448.8 R |
| 3,260,699 | 7/1966 | Schmidt | 260/448.8 R |
| 3,846,358 | 11/1974 | Roedel | 260/46.5 R |

Primary Examiner—Hosea E. Taylor
Assistant Examiner—Amelia B. Yarbrough
Attorney, Agent, or Firm—John L. Young; E. Philip Koltos; Philip L. Schlamp

[57] ABSTRACT

An improved process for preparing alkali metal siliconates wherein the improvement comprises, first substituting at least 20-90 mole percent of the chlorine groups on the silanes with hydrocarbonoxy groups, by reacting the chlorosilane with an aliphatic alcohol or alcohol and water heating the mixture to remove acid and then finally adding the alkoxylated silane to an aqueous alkali metal hydroxide solution to form the desired alkali metal siliconate.

11 Claims, No Drawings

PROCESS FOR PREPARING ALKALI METAL SILICONATES

BACKGROUND OF THE INVENTION

The present invention relates to a process for producing alkali metal siliconates and more specifically the present invention relates to an improved process for preparing alkali metal siliconates, by first alkoxylating a major portion of the chlorine groups in the chlorosiliane reactant.

Silicone resins, and silicone resin solutions, are well-known as environmental protecting agents for masonry.

Briefly, silicone resins, as is well-known, and silicone materials, as is well-known, have improved resistance to the elements and the ultra-violet rays of sunlight as well as being eminently water-repellant.

Accordingly, it was early known in the industry to prepare organic solvent, silicone resin solutions at a solid concentration of 1 to 10 percent by weight and apply any such silicone resin solutions to masonry so that the masonry would be further water repellant than was the case without such a protective coating.

However, such silicone resin organic solvent solutions were not always suitable in protecting masonry surfaces that were not very porous. Accordingly, in the case of marble and high calcium-carbonate content masonry surfaces, the use of such silicone materials did not have as many advantages as with other types of masonry surfaces. With the silicone organic solvent solutions that were applied to protect such surfaces, the silicone did not become absorbed as much as would be desired on the surface of the masonry and as a result it would tend to stay completely on the surface of the masonry.

One disadvantage of such silicone resin solution when applied to masonry surfaces with a small amount of porosity was that the silicone resin that tended to stay completely on the surface of the masonry, tended to pick up dirt which is a property of some silicone water repellants. Accordingly, there was a tendency when such non-porous masonry surface were coated with such silicone resin solutions, that such masonry surfaces would be susceptible to dirt pick up, and as a result would be susceptible to discoloration and also a greater tendency to be washed away.

Accordingly, for such non-porous, or minor porosity masonry surfaces, it was highly desirable to utilize a different type of silicone material to coat such masonry surfaces. In addition, the prior art silicone resins which were applied in the form of organic solvent solutions would unduly increase the cost of such coating solutions, as well as possibly presenting some environmental problems. In addition the prior silicone materials would not cure completely thus making them susceptible to being washed off the surface. For these reasons, it was desirable to have a silicone material which could be utilized to coat masonry surfaces which could be utilized to coat masonry surfaces which could be utilized in an aqueous solution. It was also highly desirable that such silicone material, which could be applied in an aqueous solution, be able to migrate even into minor porosity masonry surfaces and cure completely such that the coating on such masonry surfaces would not have excessive dirt pickup from the atmosphere by the silicone material and such that the silicone material would provide the proper protection to the masonry surface against the elements.

Accordingly, for this purpose and for the coating of such masonry material and fulfilling the above objects there was devised alkali metal siliconates which were formulated in aqueous solutions for the purpose of coating masonry surfaces, with the foregoing advantages mentioned previously. However, such alkali metal siliconates had one disadvantage. In their preparation, which normally required the addition of a chlorosilane and more speficially, methyltrichlorosilane to water and then subsequently to an aqueous sodium hydroxide or potassium hydroxide solution, with or without the presence of an alcohol, there resulted the formation of a gel, which gel was very difficult to purify and which gel was very difficult to re-dissolve aqueous alkali solutions so as to provide the appropriate aqueous solution of the siliconate for application to masonry surfaces.

Some of the prior art U.S. patents in preparation of such siliconate materials that should be mentioned are, for instance:

| | |
|---|---|
| Hyde et al | 2,438,055 |
| Elliott et al | 2,507,200 |
| MacMullen | 2,587,636 |
| Barry | 2,469,625 |
| Bidaud et al | 2,567,315 |
| Biefeld | 2,392,805 |
| Brick | 2,574,168 |
| Cruz, Jr. | 2,519,232 |
| Currie | 2,523,281 |
| Dennett | 2,588,365 |
| Dennett | 2,588,366 |
| Hyde | 2,439,689 |
| Krieble et al | 2,441,422 |
| Elliott et al | 2,441,423 |
| Norton | 2,386,259 |
| Norton | 2,412,470 |
| Patnode | 2,306,222 |
| Pierce | 2,500,770 |
| Rasmussen | 2,612,482 |
| Safford | 2,510,661 |
| Slayter | 2,604,688 |
| Thayer | 2,474,704 |
| Roedel | 3,846,358 |
| Agnew | 2,504,484 |

With respect to the foregoing Hyde et al Pat. No. 2,438,005 it should be noted that the chlorosilane or mono-organo trichlorosilane material is reacted with an alkali metal hydroxide in the presence of water and an alcohol in a single phase system from which complex salts containing water of crystalization, crystallized out. This method, while not specifically speaking of a gel, notes the formation of solid crystaline materials which precipate out, which not only lower the yield in the process but require subsequent purification techniques. At any rate, it was highly desirable to provide for a process of producing alkali metal siliconates in which the reactants would remain in solution and would remain in a liquid stage throughout the entire process up to the formation of the final product, such that the final product, the alkali metal siliconate, was always in solution. Such a process would obviate the need of purification and handling of a gel as was the case with the prior art processes and would eliminate the need for purification or subsequent purification steps in the removal of unwanted salts which not only would involve additional purification techniques but in addition would lower the yield from the foregoing process.

Accordingly, it is one object of the present invention to provide for an improved process for producing alkali metal siliconates wherein in the process a gel is not formed.

It is an additional object of the present invention to provide for an improved process for producing an alkali metal siliconate in which complex salts do not precipitate out and are not formed.

It is yet an additional object of the present invention to provide for an improved and more efficient process for producing alkali metal siliconates.

It is still an additional object of the present invention to provide for an improved process for preparing an alkali metal siliconate aqueous solution which is highly suitable for coating masonry surfaces.

These and other objects of the present invention are accomplished by means of the disclosure set forth herein below.

SUMMARY OF THE INVENTION

There is provided in accordance with the present invention an improved process for producing alkali metal siliconates comprising (a) adding an aliphatic alcohol to a chlorosilane, with or without the presence of water where said chlorosilane is selected from the class consisting of mono-organo chlorosilanes and tetra-chlorosilane to form a mixture such tht said chlorosilanes have at least 20 mole % of the chlorine groups on them substituted by hydrocarbonoxy groups, wherein said organic groups on said chlorosilanes are selected from the class consisting of alkyl radicals, phenyl radicals, vinyl radicals and fluoroalkyl radicals of up to 10 carbon atoms. Generally, anywhere from 20 to 90 mole percent of the chlorine groups on the chlorosilanes may be substituted by hydrocarbonoxy groups or alkoxy groups from the aliphatic alcohol, and more preferably, anywhere from 25 to 90 mole percent of the chlorine groups may be substituted by alkoxy groups. After the alkoxylation of the chlorosilane has been initiated with or without the presence of water the resulting mixture is then heated to at least 50° C. and more preferably at the reflux temperature of the chlorosilane-alcohol mixture to remove acid and drive the reaction to a greater degree of completion. Subsequent to this step which may be for any period of time the mixture is then cooled to room temperature to separate the alcohol-acid phase that remains and leave a substantially pure methoxysiloxane phase.

It is important at this juncture, that the siliconate phase have an acid content that does not exceed 10,000 ppm. If the acid content does not exceed 10,000 ppm, then excess undesirable salts will not be produced and the siliconate phase may be added to an aqueous alkali metal hydroxide solution which is preferably a potassium hydroxide or sodium hydroxide aqueous solution to form the desired solution of the alkali metal siliconate.

To form the desired alkali metal siliconate product there only remains in the process, the filtering of the final alkali metal siliconate to remove impurities and subsequent thereto to adjust the solids content to anywhere from 1 to 60 percent by weight solids and preferably 1 to 10 percent by weight of solids for masonry water repellant applications. It should be mentioned in accordance with the instant process that no gel is formed and that during the entire process the chlorosilanes, and the methoxysiloxanes as well as the siliconate that is formed remain entirely in solution.

It should also be specified that although in the above Summary of the Invention there is indicated that monoorgano chlorosilanes and tetra-chlorosilane may be utilized as the chlorosilane reactant, the most preferred reactant of course as is known in the industry is the mono-organo trichlorosilane reactant which produces the most desired alkali metal siliconate in accordance with the instant disclosure.

DESCRIPTION OF THE PREFERRED EMBODIMENT

The chlorosilanes that may be utilized in the instant process are generally selected from mono-organo chlorosilanes, specifically mono-organo tri-chlorosilanes and tetrachlorosilane. With respect to the organo group on such mono-organo chlorosilanes, it may generally be selected from monovalent hydrocarbon radicals, halogenated monovalent hydrocarbon radicals, such as alkyl radicals methyl, ethyl and propyl of up to 10 carbon atoms, mono-nuclear aryl radicals such as phenyl, methylphenyl, ethylphenyl, etc., cycloalkyl radicals such as cyclohexyl, alkenyl radicals such as vinyl, allyl, etc.; and halogenated alkyl radicals such as fluoroalkyl radicals, such as for instance, 3,3,3, trifluoropropyl. Most preferably, such organo radicals are selected from alkyl radicals of up to 10 carbon atoms, phenyl radicals of up to 10 carbon atoms, vinyl radicals and fluoro-alkyl radicals of up to 10 carbon atoms.

In the instant process, it is envisioned that for such mono-organo chlorosilanes when they are utilized as reactants in the instant process, that there may be a mixture of chlorosilanes having a different organo groups appended to the silicone atom. Generally, the alcohol is added to the chlorosilanes. Although, the chlorosilanes may be added to the alcohol for the purpose of stablizing the reaction as much as possible and preventing undue temperature build-up, it is preferable to add the aliphatic alcohol to the chlorosilane. Preferably such aliphatic alcohol has the formula R'OH where R' is an alkyl radical of one to six carbon atoms most preferably R' is methyl or ethyl since the preferred alcohols are methanol or ethanol. In addition, it is preferable that in the instant process there be utilized as a reactant a mono-organo chlorosilane and specifically either methyl trichlorosilane, ethyl trichlorosilane, propyl trichlorosilane, vinyl trichlorosilane, or phenyl trichlorosilane. The most preferred reactant of course is methyl trichlorosilane.

In the instant process sufficient alcohol is added to the chlorosilane such that at least 20 mole percent of the chlorine groups are substituted by hydrocarbonoxy groups. Preferably, 25 to 90 mole percent of the chlorine groups on the chlorosilanes is substituted by hydrocarbonoxy groups. To facilitate the substitution of hydrocarbonoxy groups for chlorine groups in the chlorosilanes it is preferred that there be present some water along with the chlorosilanes whether that water is added along with the alcohol or is added subsequent to the addition of the aliphatic alcohol.

In the most preferred embodiment of the instant invention, it is preferable that water be added along with the aliphatic alcohol to the chlorosilanes, or that the water be added subsequent to the addition of the aliphatic alcohol to the chlorosilanes.

In the most preferred embodiment of the instant case, such water that is added varies anywhere from 0 to 25 percent by weight, based on the weight of the entire aliphatic alcohol and water addition mixture. Most preferably the amount of water that is added is 5 to 21 percent by weight of the total aliphatic alcohol/water hydrolysis mixture. The reason that the amount of water that is added is not very large, is that large amounts of water will hydrolyze the chlorosilane and substitute silanol groups, which condense to form siloxanes, large amounts of which are undesirable. Further large amounts of water outside the above range may cause a reaction mixture to gel.

It is the object of the present invention and in particular the improved process of the present invention to substitute as many of the chlorine groups on the chlorosilanes as is possible with hydrocarbonoxy groups rather than with silanol groups as occurs when the chlorine group on such chlorosilanes comes in contact with water. Of course, there is the possibility that such silanol groups may further react with the alcohol to substituted alkoxy groups on the chlorosilanes. However, this reaction is much slower and what happens is that the silanol groups react with each other to form siloxanes, which are not as desirable to have in the reaction product as alkoxy groups. Accordingly, for the above reasons it is desired to have a small amount of water present in the hydrolysis reaction of the aliphatic alcohol with the chlorosilane since it facilitates the substitution of hydrocarbonoxy groups, i.e., the mixture of aliphatic alcohol and water facilitates the substitution of hydrocarbonoxy groups for chlorine groups in the chlorosilane as long as there is not present too much water.

Accordingly, for the above reasons, it is preferred that in the hydrolysis mixture that is utilized that there be a mixture of water with aliphatic alcohol in the hydrolysis of such chlorosilanes.

Accordingly, per part of chlorosilanes there may be utilized from 0.27 to 0.65 parts by weight of alcohol and 0 to 0.10 parts by weight of water.

After the mixture of aliphatic alcohol and water is added to the chlorosilanes the mixture can be stirred or agitated as is desired to promote the reaction or substitution of chlorine groups with the alkoxy groups in the chlorosilane. Generally, such addition of alcohol and water to the chlorosilanes, should take place slowly over a period of time varying from one-half hour to hour hours. Generally, during such addition procedure it is preferred that the temperature of the reaction mixture be allowed to vary at will, since this will have no affect on the product that is formed.

When the reaction has been completed, it is then desirable to heat the mixture to at least 50° C,. or above and more preferably to the reflux temperature of the alcohol so as to remove the hydrogen chloride that is formed and more effectively hydrolyze or methoxylate the chloro silyl groups. This procedure is generally continued for a period of time of anywhere from ¼ to 5 hours. After the mixture has been heated for a period of time of anywhere from ¼ to 5 hours it is then cooled, and there is formed two phases, one an alcohol/acid phase and the other phase being the alkoxylated chlorosilane. The silicone phase is separated from the alcohol-acid phase. At this time the silicone phase is tested for acid content and such that it preferably has an acid content that does not exceed 10,000 ppm. If the acid content of such silicone phase exceeds 10,000 parts per million, it is desirable to heat the mixture again at elevated temperatures until the excess acid is removed. It is undesirable to decrease the excess acid of the silicone phase by the addition of bases since such may add undesirable salts to the silicone phase and may result in the gelling of the silicone phase. It is also highly desirable in this step that the acid content in the silicone phase be controlled so that is is 10,000 ppm or less since otherwise it is possible that the alkoxylated siloxane phase forms excess salts which are undesirable in the process to be described below. As soon as the acid content of the silicone phase or the alkoxylated silicate is preferably 10,000 ppm or less, than the siloxane phase may be added to an aqueous alkali metal hydroxide solution to form the desired alkali metal siliconate.

Generally the amount of the alkoxylated silicate is added to an aqueous alkali metal hydroxide solution which contains 20 to 40 percent by weight of the alkali metal hydroxide. The most preferred alkali metal hydroxide solution being aqueous solutions of potassium and sodium hydroxide. With respect to the concentration of alkali metal hydroxide in the solution in the concentration is not critical. It is desired that the concentration not exceed 40 percent by weight of the aqueous solution since if the concentration is above 40% by weight you have to dilute the resulting product. Accordingly, it is preferred that the concentration of alkali metal hydroxide in the aqueous solution not exceed 40% by weight. As far as a minimum concentration is concerned as specified above, there is no criticality in this respect either. It is just necessary that there be sufficient alkali metal hydroxide in the aqueous solution so as to react and carry out the necessary substitution in the alkoxylated silicate to produce the desired alkali metal siliconate in accordance with the instant invention.

It is necessary in the above reaction that there be 0.9 to 1 moles of alkali metal hydroxide per mole of chloro silane since otherwise you will not obtain complete reaction and solution to the alkali metal siliconate of the silicone reactant.

Desirably this addition of the alkoxylated siloxane to the aqueous alkali metal hydroxide solution takes place at room temperature and with a time of addition which takes place in a period of time varying anywhere from one-half four to four hours. More preferably, the addition takes place in a period of time varying anywhere from one-half hour to one hour with adequate agitation.

Since the reaction is exothermic, it is desirable that the addition take place at room temperature. However, the temperature can be allowed to rise without any undue problems. Although higher temperatures for the reaction medium, such as temperatures up to 100° C. can be tolerated, it is highly desirable that by the rate of addition of the alkoxylated silicate to the alkali metal hydroxide aqueous solution that the temperature of the reaction medium be controlled. Accordingly, if the addition of the alkoxylated silicate to the aqueous alkali metal hydroxide solution is carried out under the above conditions there would result a solution of the desired alkali metal siliconate. Specifically, no gel will be formed in accordance with the instant improved process if the addition of the alkoxylated siloxane to the aqueous alkali metal hydroxide solution is carried out within the conditions set forth previously.

Within the ambient of the instant invention it has been found that even if the solution is cooled to temperatures as low as 0° F. that a gel is not formed and that a precipitate is not formed and that the only effect that is noticed is that the solution of the alkali metal siliconate becomes more viscous, which viscosity increase dissipates when the solution is heated back to room temperature or above.

However, the above ratios are again exemplary and wide variations within the above preferred weight ratio of the aqueous alkali metal hydroxide solution to the alkoxylated silicate is permissible within the instant invention.

It should also be mentioned in this instance that in accordance with the above disclosure it is disclosed that within the preferred reaction medium there are present both water and an aliphatic alcohol in the initial alkoxylation of the chlorine groups in the chlorosilane. In this instance it is highly desirable that not all of the chlorine groups in the chlorosilane be alkoxylated, and the reason for this is that if it is desired to alkoxylate all the chlorine groups in the chlorosilane in the initial step of the process not only is it necessary to use larger amounts of alcohol than those specified above resulting in undue waste, but further the reaction period is unnecessarily prolonged without any resulting advantages obtained from such complete alkoxylation of the chlorine groups in the chlorosilane reactant.

Accordingly, with the above comments, it should be noted that the desired solution of the alkali metal siliconates is then taken and filtered through a well-known filter such as Celite, a diatomaceous earth, to remove undesirable impurities and salts and then the alkali metal siliconate is adjusted to the desired solids content by either the addition of water or by the evaporation of water since the alkali metal siliconate is present in the form of an aqueous solution.

Accordingly, such product can be taken and applied to surfaces at the desired solids content, after the solids content adjustment, where there is present at a concentration of any where from 1 to 80 percent weight solids and more preferably 1 to 10 percent by weight of solids and applied to masonry surfaces to protect such masonry surfaces from the elements.

It can be appreciated that there are many variations within the scope of the instant invention that are possible, applicant having given above only his most preferred embodiment and conditions.

The examples below are given for the benefit of illustrating the practice of the improved process of the instant invention and are not given for any purpose in terms of limiting or defining the scope and definition of the instant invention. All part in the examples are by weight.

EXAMPLE 1

To 500 parts of methyltrichlorosilane in a 2—liter flask there was added a premixed blend of 166parts of methanol and 44 parts of water. The addition was made with vigorous stirring and completed in 32 minutes. The temperature dropped to $-7°$ C. following addition of 40 percent of the methanol—water blend and then warmed to 34° C. by the time addition was complete. The reaction mixture was heated to reflux (68° C.) and held at reflux for 15 minutes to further rid the system of gaseous HCl. The product was cooled and transferred to a separatory funnel. The lower siloxane rich phase (266 parts) was separated from the upper methanol—HCl phase (65 parts). The siloxane methoxylate phase had an acidity of 13,640 ppm HCl and a methoxy content of 31 weight percent. Fifty parts of the siloxane methoxylate was added to 66 parts of a 38 percent aqueous solution of sodium hydroxide in a steady stream with vigorous stirring over a time interval of 2 to 3 minutes. The mixture gave a clear solution of sodium methyl siliconate with the temperature rising to 65° C. The percent solids of the sodium methyl siliconate solution was 50 percent. The solution remained clear upon further dilution with water.

EXAMPLE 2

Fifty-three parts of the siloxane methoxylate prepared in Example 1 was added to 92 parts of a 35 percent aqueous solution of potassium hydroxide with vigorous stirring over a 3-minute period. The methoxylate immediately dispersed to give a clear solution of potassium methyl siliconate with a percent solids of 48.6.

EXAMPLE 3

To 200 parts of methyltrichlorosilane in a 1-liter flask was added with vigorous agitation a blend of 84.8 parts of methanol and 12.2 parts of water over a time period of 35 minutes. The temperature dropped to 0° C. after 40 percent of the blend of methanol-water had been added and then warmed to 36° C. by the completion of addition. The reaction mixture was heated to reflux (70° C.) and reflux for 15 minutes. Twenty parts of methanol was added and the mixture stirred 5 minutes. The pressure was reduced to 100 mm Hg and the mixture stripped to 105° C. The siloxane methoxylate had an acidity of 1450 ppm HCl and a methoxy content of 38 weight percent. This product was not dissolved in aq. NaOH, since it was evident the desired sodium metal siliconate would be obtained.

EXAMPLE 4

To 200 parts of methyltrichlorosilane in a 1-liter flask there was added with vigorous stirring a blend of 54 parts of methanol and 21 parts of water over a time period of 45 minutes. The temperature dropped to 5° C. during addition and then rose to 40° c. by completion of addition. The reaction mixture was heated to reflux (68° C.) and refluxed for 15 minutes. When 20 parts of methanol was added, a considerable amount of gel was noted as present.

I claim:

1. An improved process for producing alkali metal siliconates comprising (a) adding an aliphatic alcohol of the formula, R' OH
    wherein R' is an alkyl radical of 1 to 6 carbon atoms and water to a chlorosilane selected from the class consisting of monoorganochlorosilanes and tetrachlorosilane to form a mixture such that said chlorosilanes have from 20 to 90 mole percent of chlorine groups substituted by hydrocarbonoxy groups where said organo groups are selected from the class consisting of alkyl radicals, phenyl radicals, vinyl radicals and fluoroalkyl radicals of up to 10 carbon atoms, (b) heating the mixture to at least 50° C. to remove acid; (c) cooling the mixture and separating out the alcohol-acid phase from the siloxane phase; (d) adding the siloxane phase to a water-alkali metal hydroxide solution to form the desired alkali metal siliconate product.

2. The process of claim 1 wherein the chlorosilane is methyltrichlorosilane.

3. The process of claim 1 wherein water as well as said alcohol are added wherein the concentration of alcohol to water varies from 5 to 21% by weight of water based on the total aliphatic alcohol, water hydrolysis mixture.

4. The process of claim 3 wherein in steps (a) 30 to 90 mole percent of the chlorine groups are substituted by hydrocarbonoxy groups.

5. The process of claim 1 wherein the alcohol is methanol.

6. The process of claim 4 wherein in step (b) the mixture is heated to the reflux temperature of said alcohol.

7. The process of claim 1 wherein part of weight of chlorosilane there is added 0.27 to 0.65 parts by weight of alcohol and from 5 to 21% by weight of water based on the total aliphatic alcohol, water hydrolysis mixture.

8. The process of claim 6 wherein in step (c) the silicate phase must have an acid content that does not exceed 10,000 ppm and wherein step (b) is repeated until the foregoing acid content is obtained.

9. The process of claim 8 wherein in step (d) the water-alkali metal hydroxide solution contains from 20 to 40% by weight of said alkali metal hydroxide.

10. The process of claim 9 wherein the alkali metal hydroxide is sodium hydroxide.

11. The process of claim 10 where subsequent to step (d) further comprising filtering said alkali-metal silicate solution to remove impurities and adjusting the solids content to 1 to 60% by weight solids.

* * * * *